United States Patent [19]

Anner et al.

[11] 4,150,127

[45] Apr. 17, 1979

[54] NOVEL STEROID COMPOUNDS HAVING AN OXYGEN FUNCTION IN THE 19-POSITION

[75] Inventors: Georg Anner, Basel; Hellmut Ueberwasser; Michel Biollaz, both of Riehen; Peter Wieland, Oberwil, all of Switzerland

[73] Assignee: Ciba-Geigy Corporation, Ardsley, N.Y.

[21] Appl. No.: 838,518

[22] Filed: Oct. 3, 1977

[30] Foreign Application Priority Data

Oct. 5, 1976 [LU] Luxembourg .................. 75936
Mar. 17, 1977 [LU] Luxembourg .................. 76966

[51] Int. Cl.² .............. A61K 31/56; C07J 19/00; C07J 17/00
[52] U.S. Cl. .............. 424/238; 260/239.55 R; 260/239.57; 260/397.1
[58] Field of Search .............. 260/239.57, 239.55, 260/397.1

[56] References Cited

U.S. PATENT DOCUMENTS

| | | | |
|---|---|---|---|
| 4,028,348 | 6/1977 | Bite et al. .................. | 260/239.5 |
| 4,058,522 | 11/1977 | KeKesy et al. .................. | 260/239.57 |

*Primary Examiner*—Elbert L. Roberts
*Attorney, Agent, or Firm*—Theodore O. Groeger

[57] ABSTRACT

Novel 19-oxygenated steroids of the 20-spiroxane series of the formula

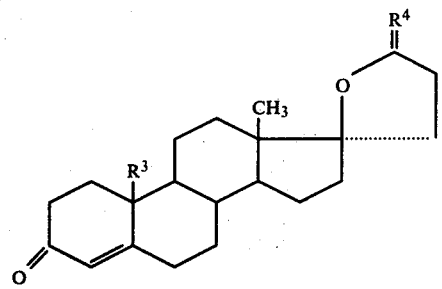

in which $R^3$ is a lower alkyl radical carrying an oxygen-containing functional group and $R^4$ is two hydrogen atoms or an oxo group, and which carry a double bond or a methylene group in the 6,7-position or carry a lower alkanoylthio group in the 7α-position, and the corresponding 17β-hydroxy-21-carboxylic acids of the formula

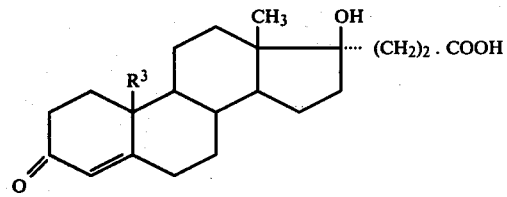

in which $R^3$ is as defined above, and which carry a double bond or a methylene group in the 6,7-position, as well as salts thereof and 1,2-dehydro derivatives of all of these compounds are advantageous as potassium-saving diuretics in therapy since they antagonize the physiological effects of aldosterone but have only slight side effects on sexual functions of the body. The compounds are obtainable by conventional general preparation processes of steroid chemistry.

28 Claims, No Drawings

NOVEL STEROID COMPOUNDS HAVING AN OXYGEN FUNCTION IN THE 19-POSITION

The invention relates to novel 19-oxygenated steroid compounds of the spiroxane series of the formula

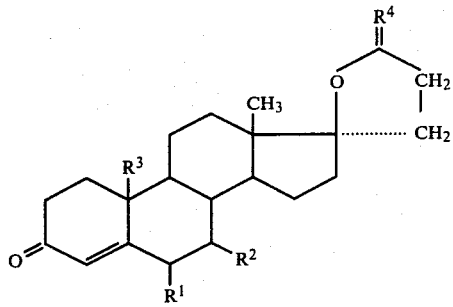

in which $R^1$ is a hydrogen atom and $R^2$ is an α-oriented lower alkanoylthio group, or $R^1$ and $R^2$ conjointly are a carbon-carbon bond or an α-oriented or β-oriented methylene group, $R^3$ is a radical of the partial formula

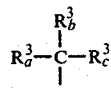

in which $R_a^3$ and $R_b^3$ each individually are a hydrogen atom or a lower alkyl radical and $R_c^3$ is a free or esterified hydroxyl group or a lower alkoxy group, or $R_a^3$ and $R_b^3$ conjointly are an oxo group, in which case $R_c^3$ is a hydrogen atom, a lower alkyl radical, a free hydroxyl group or a lower alkoxy group, and $R^4$ is two hydrogen atoms or an oxo group, and also to corresponding 17β-hydroxy-21-carboxylic acids of the 17α-pregnane series and salts thereof, in which $R^1$ and $R^2$ conjointly are a C-C bond or a methylene group and $R^3$ is as defined above, and to 1,2-dehydro derivatives of all of these compounds, and also to the preparation of all these compounds including the salts and 1,2-dehydro derivatives. The invention also relates to pharmaceutical formulations which contain the novel compounds as active components, and processes for the preparation of these formulations, as well as the therapeutic use of these compounds and formulations.

Unless otherwise indicated, the term "lower" used to qualify a compound or a substituent relates to a compound or a substituent containing not more than 7, and preferably not more than 4, carbon atoms.

An esterified hydroxyl group is derived from the carboxylic acids commonly used in steroid chemistry, for example from monocarboxylic acids having 1–18 C atoms, and especially from straight-chain or branched lower alkanoic acids, such as formic acid, propionic acid, butyric acid, isobutyric acid, valeric acid, isovaleric acid, trimethylacetic acid, hexanoic acid, 2,2-dimethylbutyric acid, heptanoic acid and, in particular, acetic acid. However, it is also possible to use acids which are unsaturated and/or substituted in a conventional manner, for example: phenylacetic acid and cyclohexylacetic acid, phenoxyacetic acid, β-cyclopentylpropionic acid, halogenoacetic acids, such as chloroacetic acid and trifluoroacetic acid, aminoacetic acid, α- or β-hydroxypropionic acid, benzoic acid and undecylenic acid, as well as lower aliphatic dicarboxylic acids, such as succinic acid and glutaric acid, in which the second carboxyl group can be in the form of a salt with an alkali metal, for example potassium or sodium.

A lower alkanoylthio group is derived especially from the said lower alkanoic acids and in particular is the acetylthio group.

A lower alkyl radical is preferably a lower alkyl radical having a straight carbon chain, for example ethyl, propyl, butyl and especially methyl. Preferred lower alkoxy radicals correspond to the said preferred lower alkyl radicals; the methoxy radical is particularly preferred.

The abovementioned 17-hydroxy-17α-pregnane-21-carboxylic acids which are characterised by the formula

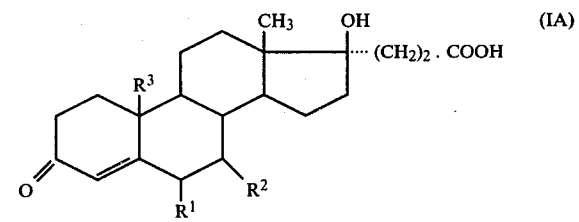

in which $R^1$, $R^2$ and $R^3$ are as defined above and in which an additional 1,2-double bond can be present, and the corresponding lactones of the formula I, in which $R^4$ is an oxo group, or the 1,2-dehydro derivatives thereof, are closely related to one another, the former being merely the hydrated form of the latter.

As already mentioned, hydroxy-acids of the formula IA in which $R^1$ and $R^2$ conjointly are a C-C bond or a methylene group, and also their corresponding 1,2-dehydro derivatives, can also be in the form of their salts.

Possible salts are, especially, metal salts and ammonium salts, such as alkali metal salts and alkaline earth metal salts, for example sodium salts, calcium salts, magnesium salts and, preferably, potassium salts, and ammonium salts derived from ammonia or a suitable, preferably physiologically acceptable, organic nitrogen-containing base. Possible bases are both amines, such as lower alkylamines, for example triethylamine, hydroxy-lower alkylamines, for example 2-hydroxyethylamine, di-(2-hydroxyethyl)-amine or tri-(2-hydroxyethyl)-amine, cycloalkylamines, for example dicyclohexylamine, or benzylamines, for example benzylamine and N,N'-dibenzylethylenediamine, and also nitrogen-containing heterocyclic compounds, for example those of aromatic character, such as pyridine or quinoline, or those having an at least partially saturated heterocyclic ring, such as N-ethylpiperidine, morpholine, piperazine or N,N'-dimethylpiperazine.

Preferred compounds amongst the compounds of the formula I and IA are those in which $R^3$ is a free or esterified hydroxymethyl group or a hydroxymethyl group etherified by lower alkyl.

Preferred compounds amongst the compounds of the formula I and IA in which $R^1$ and $R^2$ conjointly are a methylene group are those in which this methylene group is β-oriented.

Preferred compounds also include alkali metal salts, especially potassium salts, of the compounds of the formula IA in which $R^1$ and $R^2$ conjointly are a C-C bond or, especially, a methylene group.

The compounds according to the invention are distinguished by advantageous biological properties and are thus valuable pharmaceutical active compounds. In particular, they have a strong aldosterone-antagonistic action since they reduce the excessive retention of sodium and excretion of potassium caused by aldosterone. They are therefore important for use as potassium-saving diuretics in therapy.

Spiroxane derivatives having an aldosterone-antagonising action are known, cf., for example, Fieser and Fieser: Steroids; page 708 (Reinhold Publ. Corp., New York, 1959) and British Patent specification No. 1,041,534; 17β-hydroxy-21-carboxylic acids and their salts, which have an analogous action, are also known, cf., for example, U.S. Pat. No. 3,849,404. However, compounds of this type which have been employed in therapy hitherto have a considerable disadvantage in that they always have a certain sexual-specific activity which, in the case of the customary long-term therapy, sooner or later has an adverse effect. Adverse effects which are due to the anti-androgenic activity of the known anti-aldosterone formulations are particularly undesirable.

It has now been found that the 19-oxygenated steroid compounds characterised above surprisingly have these undesired side effects to a considerably lesser extent, although the advantageous anti-aldosterone action is retained. Thus, for example, in the case of 19-hydroxy-7α-acetylthio-20-spirox-4-en-3-one, the anti-aldosterone-active dose is from about 3 mg/kg administered perorally (Kagawa test with adrenalectomised male rats), whilst, on the other hand, a detectable anti-androgenic action arises only at doses of more than 60 mg/kg administered perorally [castrated rats treated with testosterone propionate].

The compounds according to the invention of the initially characterised formula I, and also the corresponding 17-hydroxy-17α-pregnane-21-carboxylic acids and their salts, and also, 1,2-dehydro derivatives of all of these compounds can be prepared in a manner which is known per se.

Thus, compounds in which $R^1$ and $R^2$ conjointly are a C-C bond, and their 1,2-dehydro derivatives, are obtained according to a general method by dehydrogenating a corresponding 6,7-saturated starting material of the formula II

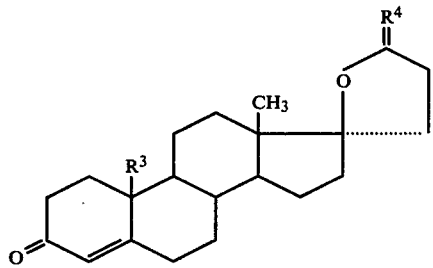

in which $R^3$ and $R^4$ are as defined above, or a corresponding 19-oxygenated 17-hydroxy-3-oxo-17α-pregn-4-ene-21-carboxylic acid, or a 1,2-dehydro derivative of these compounds, or a 3-enol ether of the 1,2-saturated compounds, in the 6,7-position and, if appropriate, also in the 1,2-position at the same time, the 3-ether group, which may be present, being split. The 6,7-dehydrogenation is carried out according to methods which are known per se, for example by treatment with a quinone having a dehydrogenating action, for example chloranil or, especially, 2,3-dichloro-5,6-dicyano-1,4-benzoquinone. When the former is used, the reaction is preferably carried out at the reflux temperature in organic solvents, for example aromatic hydrocarbons, such as benzene or xylene, lower aliphatic alcohols, such as ethanol, propanol or tert.-butyl alcohol, lower aliphatic ketones, such as acetone or 2-butanone, aliphatic esters, such as ethyl acetate, or cyclic ethers, such as dioxane or tetrahydrofurane. When dichlorodicyanobenzoquinone is used, the reaction is preferably carried out in the presence of hydrochloric acid at or below room temperature in a water-miscible organic solvent, for example one of those mentioned above.

A corresponding 3-enol ether, preferably a lower alkyl-enol ether, such as a methyl-enol ether or ethyl-enol ether, can also be reacted in an analogous manner, or, alternatively, can be dehydrogenated to the desired end product by the action of manganese dioxide, preferably in a halogenated hydrocarbon, such as chloroform or methylene chloride, the ether-forming radical being split off. The 3-ether to be used can be obtained according to generally known methods, preferably by treating a corresponding 4,5-unsaturated 3-ketone with a corresponding orthoformate, such as methyl orthoformate or ethyl orthoformate, with acid catalysis.

The simultaneous 1,2- and 6,7-dehydrogenation of the 1,2-saturated 4-en-3-one compounds or of their 3-enol ethers, which may require to be carried out, is also effected in a manner which is known per se, by treatment with a quinone having a dehydrogenating action, in particular 2,3-dichloro-5,6-dicyano-1,4-benzoquinone. Preferably, the last-mentioned reactant is allowed to act at the boil for several hours, for example 6–24 hours; solvents which can be used are the same organic solvents as have been mentioned above for the chloranil dehydrogenation.

Compounds of the formula I in which $R^1$ and $R^2$ conjointly are a double bond or a methylene group, $R^3$ is as defined above and $R^4$ is an oxo group, and also their 1,2-dehydro derivatives, can also be prepared in a manner which is known per se, by building up the lactone ring starting from corresponding 17-oxo compounds of the formula

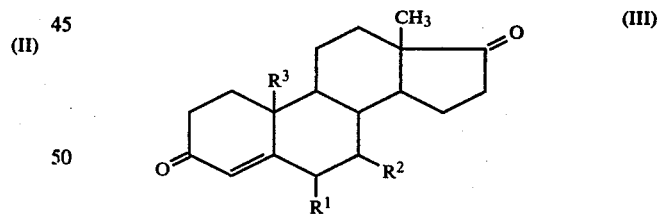

in which $R^1$ to $R^3$ are as defined immediately above, or from their 1,2-dehydro derivatives. After conventional protection of the 3-oxo group (for example in the form of the ketal or thioketal) and, where appropriate, also of an oxo group in the 19-position, the starting material of the formula III is reacted with dimethylsulphonium methylide, for example in accordance with the process described in U.S. Pat. No. 3,320,242, the resulting 17β,20-epoxy-17α-methylsteroid is subjected to a condensation reaction with the α-carbanion of a N,N-di-lower alkyl-acetamide (or with a N,N-di-lower alkyl-acetamide metallated on the methyl by an alkali metal, such as sodium or lithium) in a manner which is known per se, cf., for example, J. Org. Chem. 37, 1907–1918 (1972) and Chem. Ber. 105, 1621–1633 (1972), and a resulting N,N-di-lower alkyl-17β-hydroxy-steroid-21-carboxamide, especially a N,N-dimethyl-17β-hydroxy-steroid-21-carboxamide, is converted into the desired lactone by treatment with an acid cation exchanger, for example in accordance with the process described in German Offenlegungsschrift No. 2,424,572, the protected oxo groups being set free at the same time or subsequently.

6,7-Dehydro compounds of the formula I in which $R^1$ and $R^2$ conjointly are a C-C bond can, if desired, be converted by treatment with a lower alkane-thioacid into the corresponding end products in which $R^1$ is a hydrogen atom and $R^2$ is an α-oriented lower alkanoylthio group. The addition is effected in a manner which is known per se; preferably, the particular 6,7-dehydro compound is heated in excess thiocarboxylic acid, if desired whilst irradiating with ultraviolet light. Usually, the reaction proceeds at an adequate rate at temperatures just slightly above 50°; accordingly, it is advantageous, in the case of lower-boiling thiocarboxylic acids, for example especially of thioacetic acid, to carry out the reaction at the reflux temperature; in the case of higher-boiling thiocarboxylic acids, on the other hand, it is advantageous to keep the reaction temperature at about 90°–100° C.; the necessary reaction times can extend to several hours, but ensure adequate conversion under mild conditions. In a typical process, the product formed crystallises directly on cooling, after previously evaporating off excess reactant if necessary; if desired, however, the product can also be isolated or purified in a conventional manner, for example by chromatography. Regularly, a single isomer is formed by this addition and, on the basis of analogy with other known similar compounds, the structure indicated above ($R^1$ is hydrogen, $R^2$ is a lower alkanoylthio group in the α-position) is assigned to this isomer, in accordance with the current state of knowledge. The material data in the description relating to products of this type should, however, remain valid if a different structure should subsequently be assigned.

By adding a methylene group, the 6.7-dehydro compounds of the formula I in which $R^1$ and $R^2$ conjointly are a C-C bond, and also the corresponding 17β-hydroxy-21-carboxylic acids in the form of their salts, can, if desired, be converted into the corresponding end products in which $R^1$ and $R^2$ conjointly are the 6α,7- or, especially, 6β,7-methylene group. The addition is carried out according to methods which are known per se; however, a preferred variant to be mentioned is that in which a corresponding abovementioned 6,7-dehydro compound is reacted with dimethyloxosulphonium methylide. This variant also has the substantial advantage that it has a very high stereospecificity in the case of compounds having a free 19-hydroxyl group and gives, in the main, 6,7-methylene compounds having the preferred β-configuration of the methylene group. The reaction is, for example, appropriately carried out by treating a mineral oil dispersion of sodium hydride with trimethylsulphoxonium iodide under an inert gas, such as in a nitrogen atmosphere, and with the exclusion of moisture, and adding dimethyl sulphoxide, whereupon the formation of the dimethyloxosulphonium methylide takes place. The 6,7-unsaturated steroid starting material is added to this reagent prepared in situ in a molar ratio (reagent:steroid) of about 1:1 to 5:1. The reaction is allowed to proceed at approximately room temperature and the reaction mixture is treated with water, after which the steroid is isolated by conventional methods.

In the case of those end products which contain alkali-sensitive groups, such as lactone groups or ester groups, the decomposition of the reaction mixture is appropriately to be so carried out that the pH as far as possible remains in the neutral or weakly acid range.

If desired, the resulting compounds can be converted into one another, within the scope of the end products characterised above.

Thus, 1,2-saturated compounds can be dehydrogenated to the corresponding 1,2-dehydro derivatives in a manner which is known per se. For this purpose it is possible to use biological dehydrogenation processes, for example to effect dehydrogenation by means of the microorganisms Corynebacterium simplex or Septomyxa affinis or their enzyme systems, or the compounds can be treated with selenium dioxide in an organic solvent, for example tert.-butyl alcohol. Preferably, however, the compounds are reacted with 2,3-dichloro-5,6 dicyano-1,4-benzoquinone, for example as described above for the simultaneous 1,2- and 6,7-dehydrogenation.

Compounds in which $R^1$ and $R^2$ conjointly are a C-C bond or a methylene group and $R^4$ is an oxo group can also be converted into the corresponding 17α-hydroxy-21-carboxylic acids or salts thereof in a manner which is known per se, by hydrolysing them with an alkali metal base or alkaline earth metal base, after which the free acid can be set free by acidifying, if the free acid is desired.

The alkali metal bases and alkaline earth metal bases which are used are, for example, corresponding hydroxides, such as sodium hydroxide and especially potassium hydroxide, carbonates, such as sodium carbonate and potassium carbonate, or bicarbonates, such as sodium bicarbonate and potassium bicarbonate; mixtures of water with one or more organic solvents, preferably with those which are miscible with water, for example with lower alkanols, such as methanol, ethanol or isopropyl alcohol, with cyclic ethers, such as tetrahydrofurane or dioxane, with lower alkanones, such as acetone or 2-butanone, or with lower alkylamides of lower aliphatic carboxylic acids and, amongst the latter, especially with N,N-dimethylformamide, are appropriately used as the reaction medium. Preferably, not more than one equivalent amount of base is used and vigorous reaction conditions which could adversely affect the oxygen function in the 19-position are avoided. If an ester bond is present in the 19-position this is usually split hydrolytically simultaneously with the lactone bond, under the conditions described above, irrespective of whether the ester bond is in an acylated 19-hydroxyl group or in an esterified 19-carboxyl group.

The alkali metal salts or alkaline earth metal salts obtained in this way can be converted into the corresponding free 17β-hydroxy-21-carboxylic acids by acidifying a solution or suspension of a salt in water or in a water-containing organic solvent.

If desired, free 17β-hydroxy-21-carboxylic acids can also be converted into salts by treatment with a corresponding base; ammonium salts and salts of organic bases, for example of those mentioned initially, are advantageously prepared in this way.

The starting materials of the formula II, characterised above, and also corresponding 19-oxygenated 17β-hydroxy-3-oxo-17α-pregn-4-ene-21-carboxylic acids of the formula

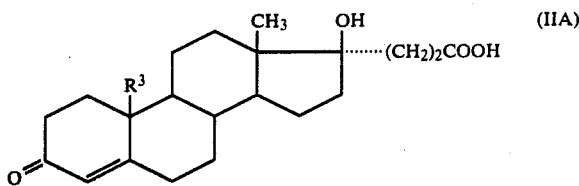

in which $R^3$ is as defined above, and salts thereof, and also the corresponding 1,2-dehydro derivatives of all of these compounds are novel and have advantageous pharmacological properties of the same type as indicated above for the end products of the formula I and IA and can be used in therapy in the same way as these end products. They are also a subject of the invention, as are the processes described below for the preparation thereof.

The compounds of the formula II and IIA are obtainable by removing the protective group in a corresponding derivative having a protected 3-oxo group, the oxo group being set free. Derivatives having a protected 3-oxo group which can be used are 3-enol ethers, 3-ketals and especially 3-thioketals. Preferred 3-enol ethers are lower alkyl-enol ethers (i.e., compounds containing the 3-(lower alkoxy)-3,5-diene grouping) and especially ethyl- and methyl-enol ethers. Preferred 3-ketals are those which are derived from lower alkanols, such as methanol or ethanol, and especially from α- or β-glycols, such as 1,2- or 1,3-propanediol, 1,2- or 2,3-butanediol and, in particular, ethylene glycol. 3-Thioketals which can be used are, especially, those which are derived from sulphur analogues of the glycols already mentioned; 3,3-ethylenedithio derivatives are particularly preferred.

These protective groups are removed in a manner which is known per se, by hydrolysis, preferably under the general conditions of acid catalysis. In the case of thioketals, the reaction is, however, preferably carried out with the addition of a sulphur-binding compound, for example of a metal salt, especially a heavy metal salt, such as cadmium carbonate and/or mercury-II chloride. Since the last-mentioned agent itself has a strongly acid reaction in the presence of water, no additional acid is necessary as the catalyst when this agent is used.

The compounds of the formula II and IIA can also be prepared, for example, by converting the methyl group in the 10β-position in 19-unsubstituted steroids of the 20-spiroxane series into an oxygen-containing radical, such as a hydroxymethyl, formyl or carboxyl group, in a manner which is known per se. Amongst the numerous methods which lead to this result, the multi-stage general process described in British Patent specifications Nos. 994,746, 994,747 and 994,749 may be mentioned as an example. In the first stage of this process a 6β-hydroxy-steroid having an unsubstituted 10β-methyl group is reacted with a lead tetraacylate, such as, in particular, lead tetraacetate, in the presence of iodine with the formation of a 6β,19-epoxy-steroid and, if desired, the latter is subsequently oxidised with a suitable strong oxidising agent, for example a derivative of hexavalent chromium, such as, in particular, with chromium trioxide in acetic acid, to give the lactone of a corresponding 6β-hydroxy-19-oic acid and this is then reduced, if desired, to the cyclic hemiacetal of a 6β-hydroxy-19-aldehyde using a di-lower alkyl-aluminium hydride, for example diisobutyl-aluminium hydride. In a further stage of the process, the 6β,19-oxygen bridge is split. In the case of the hemiacetals and lactones mentioned, this can be effected by hydrolysis; however, it is advantageous to combine the splitting of the oxygen bridge with a reductive elimination of the oxygen atom in the 6β-position. The reaction of a suitable 6β,19-epoxy-steroid with zinc is particularly suitable for this purpose: if the starting material contains a 3-oxo group besides a 4,5-double bond, the oxygen atom in the 6-position is replaced by hydrogen and the compound of the formula II or IIA is obtained direct; if the starting material to be reduced carries a halogen atom, for example a chlorine or bromine atom, in the 5α-position, a 5,6-double bond forms. If an intermediate obtained in this way has an oxo group in the 3-position, it isomerises under conventional acid or base catalysis to the desired 4,5-unsaturated 3-oxo compound of the formula II or IIA.

Alternatively, a compound of the formula II can also be prepared when, in a 5,6-unsaturated 3-hydroxy compound of the formula

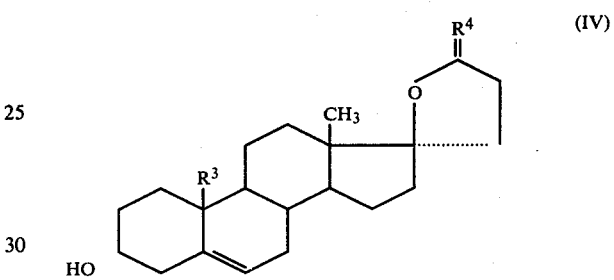

in which $R^3$ and $R^4$ are as defined above, and which is accessible by the above general process, the 3-hydroxyl group, which can be α-oriented or especially β-oriented and can be free or esterified by an easily detachable carboxylic acid, is dehydrogenated to the oxo group and, at the same time or subsequently, the 5,6-double bond is isomerised into the 4,5-position. For this reaction, oxygen-containing functional groups in the radical $R^3$ are, if necessary, temporarily protected by suitable conventional protective groups. According to a preferred two-stage process, the 3-hydroxyl group is first dehydrogenated in a manner which is known per se, for example using a compound of hexavalent chromium, such as, in particular, using chromium trioxide in aqueous sulphuric acid (Jones reagent), and the 5,6-double bond is then separately isomerised into the 4,5-position, for example by means of the abovementioned acid or basic catalysis. Another preferred alternative for the oxidation of the hydroxyl group is the Oppenauer oxidation, i.e., oxidation with a ketone, such as acetone or cyclohexanone, under the catalytic influence of an aluminium lower alkoxide, such as aluminium isopropylate. This is particularly advantageous because the 5,6-double bond migrates spontaneously into the 4,5-position with this reaction. The Oppenauer oxidation is, moreover, also successful in the case of esterified hydroxyl groups which are derived from easily detachable acids, for example formic acid, and this is important for a selective conversion, for example in the case of 3β,19-dihydroxy derivatives, where the 19-hydroxyl group is protected by esterification.

Alternatively, it is also possible to proceed in a manner which is known per se by adding bromine onto the 5,6-double bond, oxidising the 3-hydroxyl group to the 3-oxo group, for example as indicated above, and debrominating the product, for example with zinc or a chromium-II salt.

If a 1,2-dehydro derivative of the compounds of the formula II or IIA is desired, a resulting 1,2-saturated compound is dehydrogenated in a manner which is known per se, for example by means of the methods which have been indicated above for the subsequent 1,2-dehydrogenation of the compounds of the formula I.

Throughout the specification, the conventional protection of the oxygen-containing functional groups is understood to mean the conversion of a hydroxyl group or carboxyl group into an esterified form and of an oxo group into an enol ether, such as a lower alkane-enol ether, or acetal or ketal, or a thioacetal or thioketal, the protective groups being introduced and removed in a generally known manner.

In the compounds of the formula I, but especially in the starting materials of the formulae II, III and IV, the oxygenated radical $R^3$ in the 10β-position can, if desired, be converted into another radical within the scope of the definition of the symbol $R^3$; in particular, a hydroxyl group can be esterified or etherified, or an esterified hydroxyl group can be set free, a primary or secondary hydroxyl group can be dehydrogenated to an oxo group of aldehyde or ketone character, the hydroxymethyl or formyl radical can be oxidised to the carboxyl radical, the carboxyl radical can be esterified, an esterified carboxyl radical can be set free and the radical of a secondary lower alkyl- or tertiary di-lower alkyl-carbinol can be formed by adding one or two lower alkyl radicals onto a formyl, lower alkanoyl or esterified carboxyl radical. All of these conversions are effected in a manner which is known per se and can also be carried out in appropriate combinations and, if necessary, with conventional temporary protection of other functional groups which are present, such as, especially, of the 3-oxo group.

Appropriate measures which can be used to protect the 3-oxo groups are, in particular, ketalisation and the formation of enol ethers. The reactions are carried out in a manner which is known per se, especially under the conditions of acid catalysis and if necessary using dehydrating agents or azeotropic distillation. Agents used for ketalisation are, for example, lower alkanols, such as methanol or ethanol, and especially α- and β-glycols, such as 1,2- or 1,3-propanediol and 1,2- or 2,3-butanediol, and in particular ethylene glycol, or reactive derivatives of these alcohols, such as acetals or ketals, especially those in which the carbonyl component is readily volatile, for example 2,2-dimethyl-1,3-dioxolane. Analogous thioketals are obtained in an analogous manner, but starting from sulphur analogues of the abovementioned alcohols, in particular from 1,2-ethanedithiol or a reactive derivative thereof.

The reagent used to form the enol ethers is preferably an orthoester of a lower alkanol, especially of methanol or ethanol, with a lower aliphatic carboxylic acid, especially formic acid; particularly preferred reagents are methyl orthoformate and, in particular, ethyl orthoformate. The formation of the ketal or enol ether is usually accompanied by the shift of the 4,5-double bond into the 5,6-position; with the thioketals, on the other hand, this is not the case. The removal of the protective group, which follows later, can, however, always be so carried out that the double bond migrates back into its original position and the $\Delta^4$-3-oxo grouping results.

The esterification or etherification of hydroxyl groups, which is to be carried out if desired, is also effected in a manner which is known per se. For esterification, for example, the compound to be esterified is treated with an excess of the acid itself, such as with formic acid, or with a reactive derivative thereof, for example with a derivative of one of the acids indicated above, especially with an anhydride or acid halide, such as acid chloride, advantageously in the presence of a tertiary base, such as pyridine, quinoline or N-ethylpiperidine. For etherification, for example, the compounds to be etherified are treated with reactive derivatives of alcohols, for example with esters with strong acids, such as halides, sulphates or sulphonates, a possible alcohol component being, in particular, a lower alkanol, such as, in particular, methanol and ethanol. The reaction is preferably carried out in the presence of basic agents, for example metal oxides, hydroxides or carbonates, such as silver oxide, sodium hydroxide, sodium carbonate, potassium hydroxide or potassium carbonate.

The protected oxygen-containing functional groups are subsequently set free by hydrolysis, in a manner which is known per se. Acetal, ketal and enol ether groups are preferably hydrolysed under the general conditions of acid catalysis. Thioacetals and thioketals are also hydrolysed in this way, preferably as indicated above.

Esterified hydroxyl groups, whether in an acylated hydroxyl group or in an esterified carboxyl group, can also be hydrolysed under acid conditions; however, they are preferably hydrolysed under base catalysis. Basic catalysts which are used are preferably hydroxides, carbonates or bicarbonates of the alkali metals or alkaline earth metals, especially of sodium or potassium. Since the procedure is carried out under conditions analogous to those described above for the hydrolytic opening of the lactone ring, the two reactions in most cases take place simultaneously.

The optional esterification of the carboxyl group is also effected in a manner which is known per se. For example, the carboxylic acid to be esterified is treated with excess alcohol, especially one of those mentioned above, in the presence of a dehydrating agent, especially a symmetrically substituted carbodiimide, such as N,N'-dicyclohexylcarbodiimide, or of an acid catalyst, for example of a strong inorganic acid, or the free acid is first converted into a reactive derivative, such as the chloride or anhydride, and this is reacted with the desired alcohol. The esters claimed, in particular the methyl esters, can also advantageously be prepared by reacting the free carboxylic acid to be esterified with the corresponding diazo-lower alkane, in particular diazomethane.

Wherever acid catalysis is mentioned in the present specification without further specific data, this is understood as meaning treatment in the presence of an inorganic acid, for example of sulphuric acid, perchloric acid or of a hydrohalic acid, such as of hydrochloric acid, hydrobromic acid or hydroiodic acid, or, especially, of an organic acid, for example of a sulphonic acid, such as, especially, of p-toluenesulphonic acid, or of a strong carboxylic acid, such as of oxalic acid or formic acid.

A free hydroxyl group can also be oxidised to an oxo group in a manner which is known per se. Preferred oxidising agents for this reaction are compounds of hexavalent chromium, such as chromium trioxide and chromic acid and its alkali metal salts, the reaction medium used advantageously being lower alkanecarboxylic acids, such as acetic acid or propionic acid, or pyridine or acetone, which, if desired, are diluted with a halogenated lower alkane, such as dichloromethane or chloroform, and the reaction temperature preferably being kept below room temperature. The hydroxymethyl radical, which contains a primary hydroxyl group, or the formyl radical can be further oxidised to the carboxyl radical using the chromium compounds mentioned and for this purpose prolonged reaction times, temperatures at or slightly above room temperature (not above about 50° C.) and/or aqueous sulphuric acid as the solvent for the oxidising agent are appropriately used. In the same way, the formyl radical in a corresponding 17β-hydroxy-21-formyl-steroid can also be oxidised to the carboxyl group in a compound of the formula IIA.

A formyl radical, a lower alkanoyl radical, such as, in particular, an acetyl radical, and an esterified carboxyl radical, such as, in particular, the methoxycarbonyl or ethoxycarbonyl radical, in the 10β-position can be alkylated if desired. Thus a formyl radical is converted into the radical of a lower alkylcarbinol having a secondary hydroxyl group; a lower alkanoyl radical affords in this way the radical of a di-lower alkylcarbinol which has a tertiary hydroxyl group and in which the lower alkyl radicals can be identical or different, and an esterified carboxyl radical gives the radical of a tertiary di-lower alkylcarbinol in which the two lower alkyl radicals are identical. The alkylation is effected in a manner which is known per se using organo-metallic compounds as the alkylating agents. A preferred organometallic compound is a Grignard compound, for example a lower alkylmagnesium halide, such as methylmagnesium bromide or methylmagnesium iodide, or a lower alkyllithium, such as methyllithium; the solvents customary for the Grignard reaction, for example ethers, such as diethyl ether, 1,2-dimethoxyethane, tetrahydrofurane or dioxane, or hydrocarbons, such as benzene or its homologues, or mixtures thereof are used as the reaction medium. During these reactions, the oxo group in the 3-position must always temporarily be protected, preferably in the form of a thioketal.

Compounds of the formula II or IIA, and especially the corresponding derivatives having a protected 3-oxo group, can be obtained starting from corresponding 17-oxo compounds of the formula

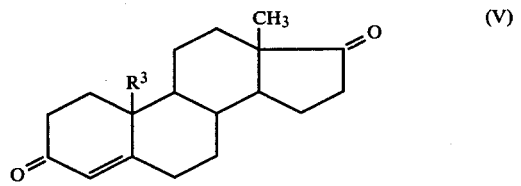

(V)

in which R³ is as defined above, according to known general processes by stepwise building-up of the spiro ring.

For this purpose the general multi-stage method which has been discussed in detail above in the context of the compounds of the formula III can be used, for example, for building up the lactone ring.

It is also possible, while temporarily protecting the oxo group in the 3-position and also the oxo group which may be present in the 19-position, to react the starting material of the formula V with a suitable organometallic compound and then to build up the desired grouping R⁴ in the spiro ring. In the case of such a variant, which preferentially results in the spirolactone ring (=20-spiroxan-21-one ring) or in the corresponding 17β-hydroxy-21-carboxylic acid, the suitable 17-oxo compound is reacted in the first stage with an ethynylorganometallic compound, especially an ethynyl-alkali metal compound, for example sodium acetylide or potassium acetylide or especially lithium acetylide. In the latter case, it is particularly advantageous to use the lithium acetylide in the form of its complex with ethylenediamine. The ethynyl radical introduced can then be carboxylated in the second stage by replacing the terminal hydrogen atom in this radical by a carboxyl group by treatment with a Grignard compound and subsequent reaction of the resulting ω-magnesium halide with carbon dioxide. During this reaction also, the other oxo groups must be protected in the manner mentioned above. In the third stage, the triple bond is then saturated in a manner which is known per se, for example by catalytic hydrogenation. This reaction is carried out with hydrogen gas under normal or elevated pressure under conditions of heterogeneous or homogeneous catalysis. Catalysts which are particularly suitable for the former are finely divided metals, for example Raney metals, such as Raney nickel, or noble metals, such as palladium, platinum or rhodium, which can, if desired, be distributed on a support, such as calcium carbonate or barium sulphate. Catalysts used for homogeneous catalysis are, in particular, complex rhodium compounds, for example tris(triphenylphosphine)-rhodium-I chloride. A 17β-hydroxy-21-carboxylic acid obtained in this way is one of the desired products, i.e., a compound of the formula IIA. It can then be converted in a manner which is known per se into a corresponding lactone of the formula II in which R⁴ is an oxo group. The lactonisation is effected under acid catalysis and/or preferably by using dehydrating agents, such as acetic anhydride, anhydrous copper sulphate or molecular sieves, or by azeotropic distillation.

According to other variants, 20-spiroxane compounds of the formula II in which R⁴ is two hydrogen atoms can be obtained in an analogous manner starting from the 17-oxo compounds of the formula V. According to a preferred general process, cf., for example, U.S. Patent Application Ser. No. 677,358, a corresponding 17-oxo compound of the formula V, in which all of the other oxo groups are in a protected form, is treated with an organometallic compound of the formula R₀-(CH₂)₃-M, in which M is a grouping MgX in which X is a halogen atom, or is an alkali metal atom, especially a lithium atom and R₀ is a di-lower alkylamino group, preferably the dimethylamino group. A 17β-hydroxy-17α-(γ-di-lower alkylaminopropyl) compound formed by this means is then converted into a corresponding quaternary tri-lower alkylammonium salt by quaternising with a lower alkyl ester of a strong acid, e.g. a lower alkyl sulphate or lower alkyl halide, such as, in particular, methyl iodide, ethyl iodide or ethyl bromide, and the corresponding quaternary base is set free from this salt by treatment with a strong base, preferably a metal hydroxide, for example silver hydroxide or an alkali metal hydroxide or alkaline earth metal hydroxide, such as potassium hydroxide, sodium hydroxide or barium hydroxide. The liberated quaternary base is then heated in an aqueous solution of a higher-boiling, water-miscible organic solvent, such as of a polyhydric alcohol, for example preferably ethylene glycol, until the ammonium group is split off by thermolysis, as a result of which the desired 20-spiroxane compound is formed.

If desired, the 21-oxo group can subsequently be introduced into the spiro ring by oxidation, for example as indicated above.

The starting materials of the formula IV can also advantageously be prepared in the same way by using corresponding 19-oxygenated 3-hydroxyandrost-5-en-17-one compounds as the starting material.

The last-mentioned compounds, and also the starting materials of the formulae III and V characterised above, are known or, if they are novel, can be obtained by obvious conventional methods, for example by the modifications of the oxygen-containing substituents $R^3$ which have been described above.

The invention also relates to those embodiments of the above process in which a compound obtainable as an intermediate at any stage is used as the starting material and the missing steps are carried out, or in which a starting material is formed under the reaction conditions.

Those compounds of the present invention which can be used pharmacologically, for example the compounds of the formulae I or IA and II or IIA, can be used, for example, for the preparation of pharmaceutical formulations, for example for the treatment of hyperaldosteronism in very diverse forms, which formulations contain an effective amount of the active substance on its own or as a mixture with inorganic or organic, solid or liquid excipients which can be used pharmaceutically, and are especially suitable for enteral, for example oral, and parenteral administration. Tablets or gelatine capsules which contain the active compound together with diluents, for example lactose, dextrose, sucrose, mannitol, sorbitol, cellulose and/or glycine, and lubricants, for example silica, talc or stearic acid or salts thereof, such as magnesium stearate or calcium stearate, and/or polyethylene glycol are preferably used; tablets also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone, and, if desired, disintegrating agents, for example starches, agar or alginic acid or a salt thereof, such as sodium alginate, enzymes of the binders and/or effervescent mixtures, or absorbents, dyes, flavourings and sweeteners. Injectable formulations are preferably isotonic aqueous solutions or suspensions; suppositories are, in particular, fatty emulsions or fatty suspensions. The pharmacological formulations can be sterilised and/or contain auxiliaries, for example preservatives, stabilisers, wetting agents and/or emulsifiers, solubilising agents, salts for regulating the osmotic pressure and/or buffers. The present pharmaceutical formulations, which, if desired, can contain further pharmacologically valuable substances, are prepared in a manner which is known per se, for example by means of conventional mixing, granulating or dragee-making processes, and contain from about 0.1% to about 75%, and especially from about 1% to 50%, of the active compound. The recommended daily dose for a warm-blooded animal weighing about 75 kg is 10–600 mg.

In the examples which follow, which further illustrate the invention without restricting it, the temperatures are given in degrees centigrade.

EXAMPLE 1

A solution of 24.0 g of 19-hydroxy-20-spirox-4-en-3-one and 19.2 g of chloranil in 670 ml of methanol is refluxed for 3 hours and evaporated to dryness in vacuo. The residue, dissolved in 400 ml of ethyl acetate, is subjected to initial purification by filtration through aluminium oxide (column 16 cm in length and 5.5 cm in diameter). The filtrate is evaporated and the crude product is further purified by chromatography on 1 kg of silica gel. The resulting 19-hydroxy-20-spiroxa-4,6-dien-3-one is crystallised from ether; melting point 149°–150°.

19-Hydroxy-20-spirox-4-en-3-one, which is used as the starting material, can be obtained as follows:

(A) 58 ml of water and 9.6 ml of 20% strength perchloric acid are added successively, at room temperature, to a solution of 80 g of 20-spirox-5-en-3$\beta$-ol acetate in 3,000 ml of acetone and the mixture is cooled to $-5°$ and treated dropwise, in the course of 6 minutes, with 32 ml of tert.-butyl hypochlorite, at $-5°$ to $-4°$, with stirring. The temperature is kept at $-5°$ for a further 50 minutes and is then kept at 0° for a further 10 minutes, during which time a clear solution results. The excess reagent is then decomposed by adding 32 ml of an approximately 40% strength aqueous solution of sodium bisulphite (KI sample negative). A solution, which has been pre-cooled to 0°, of 8 g of crystalline sodium acetate in 800 ml of water is added to the reaction mixture as a single portion in order to bring the pH value of the mixture to about 6.8 to about 7.2, and the final solution is freed from the bulk of the acetone by distilling off the latter in vacuo at a bath temperature of 25°. The concentrated reaction mixture is extracted with methylene chloride and the organic solution is dried with sodium sulphate and evaporated to dryness. On chromatography on 6 kg of silica gel, the residue gives 5$\alpha$-chloro-20-spiroxane-3$\beta$,6$\beta$-diol 3-acetate, melting point 174°–176°.

(B) 82.6 g of lead tetraacetate and 5.8 g of iodine are added to a solution of 58 g of 5$\alpha$-chloro-20-spiroxan-3$\beta$,6$\beta$-diol 3-acetate and 670 mg of $\alpha,\alpha'$-azo-bis-isobutyronitrile in 940 ml of carbon tetrachloride, under nitrogen, at 60°, and the mixture is stirred under reflux for 90 minutes. The reaction mixture is cooled to room temperature and diluted with 1,350 ml of methylene chloride and the material which has not dissolved is filtered off. The filtrate is stirred for 20 minutes with a solution of 44.6 g of sodium sulphate in 900 ml of water and for 20 minutes with 900 ml of a 30% strength sodium thiosulphate solution. On evaporation in vacuo, the organic solution gives crude 5$\alpha$-chloro-6$\beta$,19-epoxy-20-spiroxan-3$\beta$-ol acetate which, without purification, is suitable for processing in the next stage.

(C) A solution of 16.9 g of potassium carbonate in 50.7 ml of water is added to a solution of 70.9 g of crude 5$\alpha$-chloro-6$\beta$,19-epoxy-20-spiroxan-3$\beta$-ol acetate (prepared according to (B) in 43 ml of methanol and 43 ml of methylene chloride and the mixture is stirred for 3½ hours at a bath temperature of 34°–38°. The reaction mixture is concentrated to dryness in vacuo and the residue is taken up in 1,200 ml of methylene chloride. The solution is washed with several portions of a dilute solution of sodium chloride until the pH value of the wash solution is between 7 and 8 and is then dried with sodium sulphate and evaporated. Crystallisation of the residue from ether gives 5$\alpha$-chloro-6$\beta$,19-epoxy-20-spiroxan-3$\beta$-ol, melting point 175°–177°.

(D) A solution of chromic acid prepared by mixing 43.6 g of sodium dichromate dihydrate, 31.8 ml of concentrated sulphuric acid and 150 ml of water, with cooling, is added in the course of 3 minutes to a solution of 55 g of 5α-chloro-6β,19-epoxy-20-spiroxan-3β-ol in 275 ml of methylene chloride and 275 ml of dioxane, with stirring and external cooling with tap water. The reaction mixture is stirred at a bath temperature of 40° for 4½ hours, cooled to room temperature and extracted with three times 250 ml of ether. Evaporation of the ether extracts gives crude 5α-chloro-6β,19-epoxy-20-spiroxan-3-one. This is stirred for 2 hours with 55 g of potassium acetate in 260 ml of methanol at 45°, the reaction mixture is evaporated in vacuo and the residue is taken up in methylene chloride. Evaporation of the extracts in vacuo gives crude 6β,19-epoxy-20-spirox-4-en-3-one, which can be further purified by chromatography on silica gel; melting point=105°–107°.

(E) A mixture of 40.7 g of 6β,19-epoxy-20-spirox-4-en-3-one and 44 g of zinc dust in 400 ml of isopropyl alcohol, 30 ml of water and 16 ml of glacial acetic acid is stirred under reflux for 10 hours, cooled and filtered with suction. The filtrate is evaporated to dryness, the residue is dissolved in methylene chloride and a little water, the pH value is adjusted to 3 using hydrochloric acid and the organic phase is separated off. The latter is then washed with water and a dilute solution of sodium bicarbonate, dried with sodium sulphate and evaporated. Crude 19-hydroxy-20-spirox-4-en-3-one, which is thus obtained, is purified by crystallisation from a little methanol and a large amount of ether; melting point 180°–182°.

EXAMPLE 2

5 ml of thioacetic acid are added dropwise in the course of 5 minutes to a solution of 8.5 g of 19-hydroxy-20-spiroxa-4,6-dien-3-one in 25.5 ml of methanol at the boil and the mixture is stirred under reflux for a further 30 minutes. When the volatile constituents are evaporated in vacuo, a residue remains which, by chromatography on silica gel and crystallisation from methylene chloride/isopropyl ether, gives 7α-acetylthio-19-hydroxy-20-spirox-4-en-3-one with a melting point of 181°–182° (decomposition).

EXAMPLE 3

28 ml of an 8 N solution of chromium trioxide in aqueous sulphuric acid (Jones reagent) are added dropwise in the course of 15 minutes, at 0° to 8°, to a solution of 5.0 g of 19-hydroxy-20-spiroxa-4,6-dien-3-one in 450 ml of acetone and the mixture is stirred for a further 10 minutes, after which the excess oxidising agent is decomposed by adding 50 ml of methanol in the course of a further 10 minutes with external cooling. 1,000 ml of ethyl acetate are added to the reaction mixture and the chromium salts, which have separated out in the solid form, are separated off. The solution is washed twice with a saturated aqueous solution of sodium acetate, extracted twice with a saturated aqueous solution of sodium bicarbonate and also washed twice with a saturated aqueous solution of sodium chloride, dried with sodium sulphate and evaporated in vacuo. The residue is chromatographed on silica gel using a mixture of hexane/ethyl acetate (2:1); 3-oxo-20-spiroxa-4,6-dien-19-al is obtained and after recrystallisation from methylene chloride/isopropyl ether/hexane this melts at 128°–129°. The aqueous sodium bicarbonate extracts are acidified to pH 3 with hydrochloric acid and extracted several times with ethyl acetate. The organic phase is dried with sodium sulphate and concentrated and this gives 3-oxo-20-spiroxa-4,6-dien-19-oic acid, which after recrystallisation from ethyl acetate melts at 139°–141°.

EXAMPLE 4

A solution of 1.026 g of 19-hydroxy-20-spiroxa-4,6-dien-3-one in 25 ml of acetone is oxidised with 0.9 ml of an 8 N solution of chromium trioxide in aqueous sulphuric acid (Jones reagent) for 10 minutes at 5°, with stirring; the excess oxidising agent is decomposed with a few drops of isopropyl alcohol and the reaction mixture is diluted with ethyl acetate and water. The organic phase is worked up in the same way as in Example 3 and by this means 3-oxo-20-spiroxa-4,6-dien-19-al, which has a melting point of 128°–129°, is obtained as virtually the sole product.

EXAMPLE 5

A mixture of 1.04 g of 19-hydroxy-20-spirox-4-en-3-one acetate and 1.3 g of chloranil in 25 ml of methanol is refluxed in nitrogen for 3 hours and concentrated to dryness in vacuo. The residue is taken up in ethyl acetate and the solution is washed with a saturated solution of sodium dithionate in N sodium hydroxide solution and then with a saturated aqueous solution of sodium chloride, dried with sodium sulphate and evaporated in vacuo. The residue is chromatographed on silica gel; elution with a mixture of hexane/ethyl acetate (2:1) gives 19-hydroxy-20-spiroxa-4,6-dien-3-one acetate, which after crystallization from methylene chloride/isopropyl ether/hexane melts at 133°–134°.

19-Hydroxy-20-spirox-4-en-3-one acetate, which is required as the starting material, can be prepared as follows:

A solution of 500 mg of 19-hydroxy-20-spirox-4-en-3-one (prepared according to Example 1) in 2.5 ml of pyridine and 2.0 ml of acetic anhydride is left to stand for 90 minutes at room temperature and then concentrated in vacuo. The residue is dissolved in toluene and the solution is again concentrated in vacuo. The residue is chromatographed on silica gel using a mixture of hexane/ethyl acetate (3:1); after crystallization from methylene chloride/isopropyl ether/hexane, the resulting 19-hydroxy-20-spirox-4-en-3-one acetate melts at 129°–131°.

In an alternative manner, 19-hydroxy-20-spirox-4-en-3-one acetate is prepared as follows:

(A) 3.9 g of lithium cut into small pieces are stirred into a solution of 20 g of 3,3-ethylenedithio-19-hydroxy-androst-4-en-17-one in 430 ml of tetrahydrofurane, in an argon atmosphere, the mixture is cooled to 10° and a solution of 37 g of 3-chloropropanol tetrahydropyranyl ether in 40 ml of tetrahydrofurane is added dropwise in the course of 10 minutes, with stirring, the internal temperature being kept below 25° by means of a cooling bath. Stirring is continued for a further 6 hours at 20°–25°. The reaction mixture is discharged into ice-/water and taken up in methylene chloride. The organic solution is dried with sodium sulphate and evaporated in vacuo. The residue is chromatographed on silica gel; elution with a mixture of hexane/ethyl acetate (3:1) gives purified 3,3-ethylenedithio-17α-(γ-tetrahydropyran-2'-yloxypropyl)-androst-4-en-17β,19-diol in the amorphous form.

(B) A solution of 12.6 g of the last-mentioned compound in 50 ml of pyridine and 25 ml of acetic anhydride is stirred at room temperature for 90 minutes and evaporated in vacuo. The residue is chromatographed on silica gel; elution with a mixture of hexane/ethyl acetate (3:1) gives purified 3,3-ethylenedithio-17α-(γ-tetrahydropyran-2'-yloxypropyl)-androst-4-en-17β,19-diol 19-acetate in the amorphous form.

(C) 1 ml of N sulphuric acid is added to a solution of 1.1 g of the last-mentioned compound in 90 ml of acetone and the mixture is heated to the boil under reflux for 35 minutes, concentrated in vacuo at 25° and diluted with ethyl acetate. The solution is washed with a saturated solution of sodium bicarbonate and with a saturated solution of sodium chloride until neutral, dried with sodium sulphate and evaporated. The residue is chromatographed on silica gel; 3,3-ethylenedithio-17α-(γ-hydroxypropyl)-androst-4-en-17β,19-diol 19-acetate is eluted with a mixture of hexane/ethyl acetate (1:1) and with ethyl acetate and after crystallisation from methylene chloride/isopropyl ether this product melts at 154°–156°.

(D) 1.2 ml of methanesulphonyl chloride are added to a solution of 620 mg of the last-mentioned compound in 6 ml of pyridine, with external ice-cooling, and the mixture is stirred at room temperature overnight with the exclusion of moisture. The reaction mixture is discharged into ice-water and taken up in ethyl acetate and the solution is washed successively with a saturated solution of sodium bicarbonate, N hydrochloric acid and a saturated solution of sodium chloride, dried with sodium sulphate and evaporated. The oily residue is chromatographed on silica gel; elution with a mixture of hexane/ethyl acetate (9:1) gives 3,3-ethylenedithio-spirox-4-en-19-ol acetate, which after recrystallisation from ether/hexane melts at 156°–168°.

(E) A solution of 200 mg of mercuric chloride in 1 ml of water is added to a solution of 200 mg of the last-mentioned compound in 20 ml of acetone and this is followed by the addition of 200 mg of cadmium carbonate. After stirring for 4 hours at room temperature, the solid constituents are removed by filtration, the filtrate is concentrated at room temperature and the residue is taken up in ethyl acetate. The solution is filtered, washed twice with water, dried with sodium sulphate and evaporated. Chromatography on silica gel and elution with a mixture of hexane/ethyl acetate (4:1) gives 19-hydroxy-20-spirox-4-en-3-one acetate, which after recrystallisation from isopropyl ether/hexane melts at 128°–129° and is identical to the product obtained from the alternative preparation process.

EXAMPLE 6

A solution of 3.2 g of 19-hydroxy-20-spiroxa-4,6-dien-3-one acetate in 140 ml of methanol is mixed with a solution of 4.5 g of sodium bicarbonate in 55 ml of water and the mixture is stirred at the boil for 2 hours under an argon atmosphere and then concentrated in vacuo. The residue is partitioned between ethyl acetate and water and the organic phase is washed with a saturated solution of sodium chloride, dried with sodium sulphate and evaporated. The residue, dissolved in a mixture of hexane/ethyl acetate (2:1), is purified by filtering through a short column of silica gel and is then crystallised from isopropyl ether. The resulting 19-hydroxy-20-spiroxa-4,6-dien-3-one, which has a melting point of 153°–154°, is identical to the product obtained according to Example 1.

EXAMPLE 7

A mixture of 360 mg of 19-hydroxy-20-spirox-4-ene-3,21-dione acetate and 540 mg of chloranil in 9 ml of methanol is heated to the boil under reflux for 9 hours in a stream of nitrogen and then evaporated in vacuo. The residue is taken up in ethyl acetate and the solution is washed twice with a saturated solution of sodium dithionite in N sodium hydroxide solution and once with a 15% strength aqueous solution of sodium chloride, dried with sodium sulphate and evaporated in vacuo. The residue is chromatographed on 11 g of silica gel; 19-hydroxy-20-spiroxa-4,6-diene-3,21-dione acetate is eluted with a mixture of toluene/ethyl acetate (88:12), and after recrystallisation from methylene chloride/ether/acetone this product melts at 190°–191.5°.

19-Hydroxy-20-spirox-4-ene-3,21-dione acetate, which is required as the starting material, can be prepared as follows:

(A) 390 mg of lithium cut into small pieces are stirred into a solution of 2 g of 3,3-ethylenedithio-19-hydroxy-androst-4-en-17-one in 42 ml of tetrahydrofurane. A solution of 2.89 g of β-chloropropionaldehyde ethylene-acetal in 3.8 ml of tetrahydrofurane is then added dropwise to the reaction mixture, with stirring, the internal temperature being kept below 7° by external cooling, and stirring is continued for 2 hours at 0° and for 16 hours at 20°–22°. The mixture is freed from unconsumed lithium by filtering and washing the solids filtered off with toluene, the filtrate is poured onto ice and the mixture is subjected to steam distillation for 30 minutes and extracted with methylene chloride. The organic extracts are washed with a saturated aqueous solution of sodium chloride, dried with sodium sulphate and evaporated in vacuo. The residue is chromatographed on 60 g of aluminium oxide (activity II). The resulting crude product is recyrstallised from acetone/ether/petroleum ether; the resulting 17α-(3',3'-ethylenedioxypropyl)-3,3-ethylenedithio-androst-4-ene-ene-17β,19-diol melts at 163°–167°.

(B) The compound already mentioned is dissolved in pyridine and an equal amount by weight of acetic anhydride is added. After standing for 2 hours, the reaction mixture is processed in the customary manner and by this means 17α-(3',3'-ethylenedioxypropyl)-3,3-ethylenedithio-androst-4-ene-17β,19-diol 19-acetate with a melting point of 151.5°–153° is obtained.

(C) A mixture of 570 mg of 17α-(3',3'-ethylenedioxypropyl)-3,3-ethylenedithio-androst-4-ene-17α,19-diol 19-acetate, 620 mg of mercuric chloride and 620 mg of cadmium carbonate in 50 ml of acetone and 2.5 ml of water is stirred for 15 hours, 114 mg of mercuric chloride and 114 mg of cadmium carbonate are added and the mixture is stirred for a further 50 hours. Solid constituents are removed by filtering through celite and washing with acetone and the filtrate is evaporated in vacuo. 0.56 ml of N sulphuric acid is added to a solution of the residue in 50 ml of acetone, the mixture is heated to the boil under reflux for 45 minutes and cooled to 0° and 4 ml of an 8 N solution of chromium trioxide in aqueous sulphuric acid (Jones reagent) is added dropwise in the course of 5 minutes, with stirring. After a further 10 minutes at 0°, excess oxidising agent is decomposed by adding 5.6 ml of methanol and the reaction mixture is diluted with ethyl acetate, washed with a saturated aqueous solution of sodium acetate, dried with sodium sulphate and evaporated in vacuo. The residue is taken up in methylene chloride and the solution is filtered through 7.6 g of aluminium oxide (activity II) and evaporated; the resulting crude product is purified by recrystallisation from methylene chloride/ether and by this means 19-hydroxy-20-spirox-4-ene-3,21-dione acetate with a melting point 190°–191° is obtained.

Alternatively, 19-hydroxy-20-spirox-4-ene-3,21-dione can also be obtained as follows:

(A′) 19.41 g of 5β,6β-epoxy-3β-hydroxy-20-spiroxan-21-one acetate are added to 55.5 ml of a 1 percent strength (weight/volume) solution of p-toluenesulphonic acid in glacial acetic acid, with stirring. After 30 minutes, the mixture is poured into ice-water and the precipitate is filtered off with suction, washed with water and dissolved in methylene chloride. After separating off the water, the organic solution is dried and evaporated in vacuo. The residue is chromatographed on 200 g of silica gel and eluted with a mixture of toluene/ethyl acetate (19:1). Crystallisation from methylene chloride/ether gives 3β,5α,6β-trihydroxy-20-spiroxan-21-one 3,5-diacetate; melting point 227°–232°.

(B′) A mixture of 2.47 l of cyclohexane, 617 ml of methylene chloride, 140.5 g of lead tetraacetate and 65.1 g of calcium carbonate is heated to the boil for 15 minutes, with stirring, 32.55 g of iodine are added and the mixture is allowed to boil for a further five minutes. 34.28 g of the diacetate obtained above are then added and the mixture is allowed to boil, with stirring, for 30 minutes, while exposed to a 500 Watt lamp, and filtered hot through celite. The filter residue is then washed with a mixture of cyclohexane/methylene chloride (4:1). The filtrate is washed with sodium thiosulphate solution and water, dried and evaporated in vacuo.

(C′) The resulting crude 6β,19-epoxy-3β,5α-dihydroxy-20-spiroxan-21-one diacetate is dissolved in 180 ml of methanol. After adding 25 ml of 3.8 N hydrochloric acid in isopropanol, the solution is allowed to stand at room temperature for 6 hours and is poured into ice/water and extracted with methylene chloride. The extract is washed with sodium bicarbonate solution and water, dried and evaporated in vacuo. The residue is chromatographed on 1 kg of silica gel using a mixture of toluene/ethyl acetate (1:1) and by this means 6β,19-epoxy-3β,5α-dihydroxy-20-spiroxan-21-one 5-acetate is obtained.

(D′) 1.41 ml of 8 N chromic acid in dilute sulphuric acid are added to a solution of 1.15 g of the 6β, 19-epoxy compound, thus obtained, in 44.8 ml of acetone and 11.2 ml of methylene chloride, with ice-cooling and stirring. After 30 minutes, 2.27 g of sodium acetate in 44.8 ml of water are added to the mixture and the resulting mixture is extracted with methylene chloride. The methylene chloride extracts are washed with saturated sodium bicarbonate solution and water, dried and evaporated in vacuo. After crystallisation from ethanol, the residue gives 6β,19-epoxy-5α-hydroxy-20-spiroxane-3,21-dione acetate; melting point 172°–175°.

(E′) A solution of 20 g of 6β,19-epoxy-5α-hydroxy-20-spiroxane-3,21-dione acetate in 400 ml of ethanol is added to a mixture of 200 g of zinc dust, 20 g of zinc chloride and 100 ml of ethanol and the resulting mixture is allowed to reflux for 6 hours, with stirring. After cooling, methylene chloride is added to the mixture, the precipitate is filtered off with suction and the solid filtered off is washed with methylene chloride and water. The methylene chloride phase of the filtrate is separated off, washed with dilute hydrochloric acid, dried and evaporated in vacuo. Crystallisation of the residue from methylene chloride/acetone/ether with the addition of carboraffin gives 19-hydroxy-20-spirox-4-ene-3,21dione; melting point 199°–199.5°. This is identical to the product obtained from saponification of the 19-hydroxy-20-spirox-4-ene-3,21-dione acetate described above under (C) with aqueous-methanolic sodium bicarbonate solution.

EXAMPLE 8

A solution of 211 mg of sodium bicarbonate in 2.6 ml of water is added to a solution of 107 mg of 19-hydroxy-20-spiroxa-4,6-diene-3,21-dione acetate in 6.5 ml of methanol and the mixture is heated to the boil under reflux for 2 hours, treated with 0.5 ml of glacial acetic acid and evaporated in vacuo. A solution of the residue in ethyl acetate is washed with a 15% strength aqueous solution of sodium chloride, dried with sodium sulphate and evaporated in vacuo. The residue is taken up in a mixture of toluene/ethyl acetate (4:1) and the solution is filtered through 1 g of silica gel and evaporated in vacuo. The crude product is recrystallised from acetone/ether and by this means 19-hydroxy-20-spiroxa-4,6-diene-3,21-dione with a melting point of 197°–198° is obtained.

EXAMPLE 9

A solution of 680 mg of 19-hydroxy-20-spiroxa-4,6-diene-3,21-dione in 12 ml of methanol and 1.02 ml of thioacetic acid is refluxed for two hours and cooled, 5 ml of water are added and the resulting mixture is left to stand at room temperature for 5½ hours and further diluted with 200 ml of water. The precipitate is filtered off with suction, washed with water, dried in a vacuum desiccator over phosphorus pentoxide and chromatographed on 15 g of silica gel. 7α-Acetylthio-19-hydroxy-20-spirox-4-ene-3,21-dione, which has a melting point of 235°–238° (recrystallisation from methylene chloride/ether/acetone), is eluted with a mixture of toluene/ethyl acetate (4:1).

EXAMPLE 10

A mixture of 1.36 g of 19-hydroxy-20-spiroxa-4,6-diene-3,21-dione acetate, 24 ml of methanol and 2.04 ml of thioacetic acid is allowed to reflux for 2 hours. 10 ml of water are then added to the cooled reaction solution and the resulting mixture is stirred at room temperature for 7½ hours and diluted with 400 ml of water. The precipitate is filtered off with suction, washed with water and dissolved in methylene chloride. The organic solution is separated off from the water, dried and evaporated in vacuo. After chromatography on 30 g of silica gel using a mixture of toluene/ethyl acetate (9:1), 7α-acetylthio-19-hydroxy-20-spirox-4-ene-3,21-dione acetate is obtained; melting point 230°–234° (recrystallisation from methylene chloride/ether/acetone).

EXAMPLE 11

(A) A solution of 1 g of 19-hydroxy-20-spiroxa-4,6-diene-3,21-dione and 1.4 g of triphenylmethyl chloride in 30 ml of pyridine is refluxed for 20 hours in a stream of nitrogen. After cooling, the mixture is poured into ice water and 30 ml of glacial acetic acid and extracted several times with methylene chloride. The residue obtained from the organic solutions, which are washed with dilute sodium chloride solution, dried and evaporated in vacuo, is chromatographed on 30 g of silica gel. Using mixtures of toluene/ethyl acetate (49:1) to (19:1), 19-trityloxy-20-spiroxa-4,6-diene-3,21-dione is eluted in the form of a yellow foam.

(B) 2.23 g of trimethylsulphoxonium iodide are added to a mixture, which has been stirred for 30 minutes in a stream of nitrogen, of 14.5 ml of dimethylsulphoxide and 785 mg of a 55 percent strength paste of sodium hydride in oil. After 1½ hours, a solution of the trityl ether obtained above in 22 ml of dimethylsulphoxide is added to this mixture and the trityl ether solution is rinsed in with 14 ml of dimethylsulphoxide. After 23 hours the mixture is poured into a mixture of icewater and 6.65 ml of glacial acetic acid and extracted with methylene chloride. The extract is washed with dilute sodium chloride solution, dried and evaporated in vacuo.

(C) The resulting crude 6$\beta$,7$\beta$-methylene-19-trityloxy-20-spirox-4-ene-3,21-dione and 100 ml of 80 percent strength acetic acid are warmed to 75° for 30 hours, the mixture is evaporated in vacuo, toluene is added and the resulting mixture is again evaporated in vacuo. The residue is allowed to stand with a mixture of 30 ml of pyridine and 30 ml of acetic anhydride for 1½ hours at room temperature. After evaporating in vacuo, dissolving the residue in toluene and again evaporating the solution in vacuo, the product is chromatographed on 30 g of silica gel. 19-Hydroxy-6$\beta$,7$\beta$-methylene-20-spirox-4-ene-3,21-dione acetate is eluted with a mixture of toluene/ethyl acetate (19:1).

(D) A solution of 422 mg of sodium bicarbonate in 5.16 ml of water is added to a solution of 265 mg of 19-hydroxy-6$\beta$,7$\beta$-methylene-20-spirox-4-ene-3,21-dione acetate in 13 ml of methanol and the mixture is allowed to reflux for three hours in a steam of nitrogen. After adding 1 ml of glacial acetic acid, the mixture is evaporated in vacuo, water is added to the residue and the resulting mixture is extracted several times with ethyl acetate. The ethyl acetate solution is washed with dilute sodium chloride solution, dried and evaporated in vacuo. The residue is warmed with 80 percent strength acetic acid to 60° for one hour, the mixture is evaporated in vacuo, the residue is dissolved in toluene and the toluene solution is again evaporated in vacuo and the residue is subjected to preparative separation by thin layer chromatography in the system chloroform/acetone (4:1) on silica gel (PF 254). This gives 19-hydroxy-6$\beta$,7$\beta$-methylene-20-spirox-4-ene-3,21-dione; melting point 207°–208.5° (recrystallisation from methylene chloride/ether/acetone).

EXAMPLE 12

A mixture of 500 mg of 19-hydroxy-20-spiroxa-4,6-diene-3,21-dione acetate, 630 mg of 2,3-dichloro-5,6-dicyano-benzoquinone and 20 ml of dioxane is refluxed for 18 hours in a stream of nitrogen and, after cooling, is poured into 194 ml of saturated sodium bicarbonate solution and ice, with stirring. After 15 minutes, the mixture is extracted with methylene chloride and the extracts are washed with dilute sodium chloride solution, dried and evaporated in vacuo. After chromatography of the residue on silica gel, 19-hydroxy-20-spiroxa-1,4,6-triene-3,21-dione acetate is obtained; melting point 227°–229.5° (recrystallisation from methylene chloride/ether/acetone).

EXAMPLE 13

0.6 ml of an 8 N solution of chromium trioxide in aqueous sulphuric acid are added, at 0°, to a solution of 712 mg of 19-hydroxy-20-spiroxa-4,6-diene-3,21-dione in 17 ml of acetone, with stirring. 10 minutes later, excess oxidising agent is reduced with isopropyl alcohol, water is added to the reaction mixture and the mixture is extracted with ethyl acetate. The extract is washed with sodium bicarbonate solution and sodium chloride solution, dried and evaporated in vacuo. Recrystallisation of the residue from acetone/ether gives 3,21-dioxo-20-spiroxa-4,6-dien-19-al with a melting point of 173°–176.5°.

EXAMPLE 14

A solution of 680 mg of 3,21-dioxo-20-spiroxa-4,6-dien-19-al in 12 ml of methanol and 1.02 ml of thioacetic acid is allowed to reflux for two hours and, after cooling and adding 5 ml of water, is stirred for a further 22½ hours at room temperature. The reaction mixture is poured into water and the solid precipitate which has separated out is filtered off with suction and dried in a vacuum desiccator over phosphorus pentoxide. The crude product thus obtained is purified by chromatography on 25 g of silica gel. 7$\alpha$-Acetylthio-3,21-dioxo-20-spirox-4-en-19-al is obtained from the fractions eluted with a mixture of toluene/ethyl acetate (94:6) and after recrystallisation from methylene chloride/ether/acetone this product melts at 205°–209.5°.

EXAMPLE 15

1.94 ml of an 8 N solution of chromic acid in aqueous sulphuric acid is added to a solution of 620 mg of 19-hydroxy-20-spiroxa-4,6-diene-3,21-dione in 19.4 ml of acetone, with stirring and ice-cooling. After 3½ hours, isopropyl alcohol and then dilute sodium chloride solution are added to the reaction mixture and the resulting mixture is extracted with methylene chloride. The extract is washed with dilute sodium chloride solution, dried and evaporated in vacuo at 30°. The resulting crystalline 3,21-dioxo-20-spiroxa-4,6-dien-19-oic acid is dissolved in 20 ml of methylene chloride and an ethereal solution of diazomethane is added at 0°. Excess diazomethane is decomposed with glacial acetic acid, the reaction mixture is poured into sodium bicarbonate solution and the resulting mixture is extracted with methylene chloride. The organic solutions are washed with dilute sodium chloride solution, dried and evaporated in vacuo. After chromatography on silica gel, methyl 3,21-dioxo-20-spiroxa-4,6-dien-19-oate is obtained; melting point above 270° (recrystallised from methylene chloride/ether).

EXAMPLE 16

A solution of 580 mg of methyl 3,21-dioxo-20-spiroxa-4,6-dien-19-oate in 21 ml of methanol and 1.8 ml of thioacetic acid is refluxed for three hours and cooled, 8.8 ml of water are added and the mixture is left to stand for 18 hours at room temperature. After diluting with 400 ml of water, the precipitate which has separated out is filtered off with suction and washed with water. The residue on the suction filter is dissolved in methylene chloride, the aqueous layer is separated off and the methylene chloride solution is dried nd evaporated in vacuo. The residue is subjected to preparative separation by thin layer chromatography on silica gel in the system toluene/acetone (7:3). Crystallisation from methylene chloride/ether/acetone gives methyl 7$\alpha$-acetylthio-3,21-dioxo-20-spirox-4-en-19-oate with a melting point of 216°–221°.

EXAMPLE 17

A mixture of 150 mg of methyl 3,21-dioxo-20-spiroxa-4,6-dien-19-oate, 12 ml of dioxane and 378 mg of 2,3-dichloro-5,6-dicyano-benzoquinone is allowed to reflux for 23 hours in a stream of nitrogen. The mixture is poured into saturated sodium bicarbonate solution and extracted with methylene chloride; the extract is washed with dilute sodium chloride solution, dried and evaporated in vacuo. The residue is applied to 12 g of silica gel and eluted with a mixture of toluene/ethyl acetate (93:7) and by this means methyl 3,21-dioxo-20-spiroxa-1,4,6-trien-19-oate is obtained; melting point 254°–256° (recrystallisation from methylene chloride/ether).

EXAMPLE 18

A mixture of 384 mg of 19-hydroxy-20-spiroxa-4,6-dien-3-one acetate, 6 ml of methanol and 0.6 ml of thioacetic acid is allowed to reflux for 5 hours. 2 ml of water are then added to the cooled reaction solution and the resulting mixture is stirred for 16 hours at room temperature and then evaporated in vacuo. After chromatography on silica gel using a mixture of hexane/ethyl acetate (4:1), 7α-acetylthio-19-hydroxy-20-spirox-4-en-3-one acetate is obtained; melting point 67°–73° (precipitation from a methanolic solution by adding water).

EXAMPLE 19

A solution of 340 ml of 3-oxo-20-spiroxa-4,6-dien-19-al in 6 ml of methanol and 0.6 ml of thioacetic acid is allowed to reflux for one hour and, after cooling and adding 2.5 ml of water, is stirred for a further 4 hours at room temperature. The reaction mixture is then evaporated in vacuo and purified by chromatography on silica gel. 7α-Acetylthio-3-oxo-20-spirox-4-en-19-al is obtained from the fractions eluted with a mixture of hexane/ethyl acetate (4:1) and after recrystallisation from methylene chloride/diisopropyl ether this product melts at 183°–185°.

EXAMPLE 20

A solution of 1.4 g (19R)-19-hydroxy-19-methyl-20-spirox-4-en-3-one acetate and 4.4 g of chloranil in 36 ml of methanol is refluxed for 8 hours and concentrated. The residue is taken up in ethyl acetate and the solution is washed with a solution of sodium hyposulphite in 1 N sodium hydroxide solution until the aqueous phase remains virtually colourless, and is then washed twice with water and once with a solution of sodium chloride, dried and evaporated. The crude (19R)-19-hydroxy-19-methyl-20-spiroxa-4,6-dien-3-one acetate is chromatographed on silica gel using a mixture of hexane/ethyl acetate (3:1) and crystallised from methylene chloride/diisopropyl ether/hexane; melting point 184°–185°.

(19R)-19-Hydroxy-19-methyl-20-spirox-4-en-3-one acetate, which is used as the starting material, can be prepared as follows:

(A) 10 g of sodium bicarbonate in 100 ml of distilled water are added to a solution of 12.2 g of 3,3-ethylenedithio-20-spirox-4-en-19-ol acetate and 1 l of methanol, under argon, and the mixture is then refluxed under argon for 4 hours. For working up, the reaction mixture is concentrated in a rotary evaporator, poured into ice/water and taken up in methylene chloride. The organic phase is separated off, dried and evaporated. The crude product is chromatographed on silica gel using mixtures of hexane/ethyl acetate (9:1) and (4:1). The resulting 3,3-ethylenedithio-20-spirox-4-en-19-ol crystallises from acetone/hexane and melts at 128°–130°.

(B) A solution of 2.0 g of 3,3-ethylenedithio-20-spirox-4-en-19-ol in 40 ml of dimethylsulphoxide and 40 ml of acetic anhydride is stirred at room temperature for 16 hours and then evaporated under a high vacuum. The residue is taken up in ethyl acetate and the solution is washed twice with water, dried and evaporated. The crude product is chromatographed on silica gel using a mixture of hexane/ethyl acetate (95:5). The resulting 3,3-ethylenedithio-20-spirox-4-en-19-al is recrystallised from acetone/hexane; melting point 145°–149°.

(C) 180 ml of an approximately 4.4% strength solution of methyllithium in ether is added dropwise to a solution of 19.0 g of 3,3-ethylenedithio-20-spirox-4-en-19-al in 360 ml of absolute tetrahydrofurane, under argon and with ice/water-cooling, at such a rate that the internal temperature of 30° is not exceeded. The reaction mixture is then stirred for a further 15 minutes and cooled to 10°, 10 ml of an aqueous solution of ammonium chloride are added carefully and the mixture is extracted with ethyl acetate. The organic phase is washed with dilute hydrochloric acid and twice with water, dried and evaporated. The crude product is chromatographed on silica gel using mixtures of hexane/ethyl acetate (9:1) and (4:1). Amorphous (19R)-3,3-ethylenedithio-19-methyl-20-spirox-4-en-19-ol is first eluted and this is followed by (19S)-3,3-ethylenedithio-19-methyl-20-spirox-4-en-19-ol, which crystallises from diethyl ether/hexane; melting point 135°–142°.

(D) A solution of 2.5 g of (19R)-3,3-ethylenedithio-19-methyl-20-spirox-4-en-19-ol in 14 ml of pyridine and 7 ml of acetic anhydride is left to stand for 24 hours and concentrated under a high vacuum. The residue is taken up in ethyl acetate, the solution is washed with 1 N potassium bicarbonate solution, dried and evaporated and the residue, as a solution in hexane/ethyl acetate (4:1) is filtered through a short silica gel column. The (19R)-3,3-ethylenedithio-19-methyl-20-spirox-4-en-19-ol acetate which is isolated is further processed without additional purification.

(E) 13 ml of water, 2.5 g of cadmium carbonate and 2.5 g of mercuric chloride are added to a solution of 2.5 g of (19R)-3,3-ethylenedithio-19-methyl-20-spirox-4-en-19-ol acetate in 200 ml of acetone. This mixture is stirred at room temperature for 20 hours and filtered through celite. The filtrate is concentrated, the residue is taken up in ethylene chloride and the solution is again filtered through celite and evaporated. The crude ketone is chromatographed on silica gel using a mixture of hexane/ethyl acetate (3:1). The resulting (19R)-19-hydroxy-19-methyl-20-spirox-4-en-3-one acetate is crystallised from methylene chloride/diisopropyl ether; melting point 162°–164°.

EXAMPLE 21

0.6 ml of distilled thioacetic acid is added to to a solution of 342 mg of (19R)-19-hydroxy-19-methyl-20-spiroxa-4,6-dien-3-one acetate in 6 ml of methanol, the mixture is refluxed for 5 hours and cooled, water is added in an amount such that the solution becomes turbid and the solution is stirred overnight. The reaction mixture is concentrated, the residue is taken up in methylene chloride and the solution is washed once with water, dried and evaporated. The residue is chromatographed on silica gel using a mixture of hexane/ethyl acetate (4:1). The fractions containing a single compound are taken up in methanol/water and lyophilised. Amorphous (19R)-7α-acetylthio-19-hydroxy-19-methyl-20-spirox-4-en-3-one acetate is obtained.

EXAMPLE 22

A mixture of 11.53 g of (19S)-19-hydroxy-19-methyl-20-spirox-4-en-3-one acetate and 40 g of chloranil in 300 ml of methanol is refluxed for 4 hours and then concentrated. The residue is taken up in ethyl acetate and the solution is washed with a solution of sodium dithionite in 1 N sodium hydroxide solution until the aqueous phase remains virtually colourless and is then washed twice with water and once with sodium chloride solution and evaporated and the residue is chromatographed on silica gel using a mixture of hexane/ethyl acetate (9:1). The resulting (19S)-19-hydroxy-19-methyl-20-spiroxa-4,6-dien-3-one acetate crystallises from methylene chloride/diisopropyl ether and melts at 167°–168°.

(19S)-19-Hydroxy-19-methyl-20-spirox-4-en-3-one acetate, which is used as the starting material, can be obtained as follows.

(A) 50 ml of acetic anhydride are added to a solution of 20 g of (19S)-3,3-ethylenedithio-19-methyl-20-spirox-4-en-19-ol (c.f. Example 20, A to C) in 100 ml of pyridine and the mixture is left to stand at room temperature for 24 hours and concentrated under a high vacuum. The residue is taken up in ethyl acetate, the solution is washed with 1 N potassium bicarbonate solution, dried and evaporated and the residue, as a solution in hexane/ethyl acetate (4:1), is filtered through a short silica gel column. The (19S)-3,3-ethylenedithio-19-methyl-20-spirox-4-en-19-ol acetate isolated is further processed without additional purification.

(B) 85 ml of water, 17.6 g of cadmium carbonate and 17.6 g of mercuric chloride are added to a solution of 17.6 g of (19S)-3,3-ethylenedithio-19-methyl-20-spirox-4-en-19-ol acetate in 1,200 ml of acetone and the mixture is stirred at room temperature for 20 hours. For working up the reaction mixture is filtered through kieselguhr, the filtrate is concentrated, the residue is taken up in methylene chloride and the organic solution is again filtered through dieselguhr and evaporated. The residue, as a solution in methylene chloride, is filtered through aluminum oxide (activity III, neutral). The resulting (19S)-19-hydroxy-19-methyl-20-spirox-4-en-3-one acetate is recrystallised from methylene chloride/diisopropyl ether; melting point 148°–149°.

EXAMPLE 23

0.6 ml of distilled thioacetic acid is added to a solution of 398 mg of (19S)-19-hydroxy-19-methyl-20-spiroxa-4,6-dien-3-one acetate in 6 ml of methanol, the mixture is refluxed for 2 hours and cooled, water is added in an amount such that the solution becomes turbid and the solution is stirred for 2 hours. The reaction mixture is evaporated. The residue is chromatographed on silica gel using a mixture of hexane/ethyl acetate (4:1). The fractions containing a single compound are crystallised from methylene chloride/diisopropyl ether. This gives (19S)-7α-acetylthio-19-hydroxy-19-methyl-20-spirox-4-en-3-one acetate; melting point 173°–174°.

EXAMPLE 24

A mixture of 1.65 g of 19-hydroxy-20-spiroxa-4,6-dien-3-one, 7 ml of pyridine and 3.5 ml of butyric anhydride is stirred overnight at room temperature and evaporated under a high vacuum. The residue is dissolved in a mixture of acetone and ethyl acetate. Sodium bicarbonate is added to this solution and the mixture is stirred vigorously for 2 hours, diluted with ethyl acetate, washed with water, dried and evaporated. The crude product is chromatographed on silica gel using a mixture of hexane/ethyl acetate (4:1); pure 19-hydroxy-20-spiroxa-4,6-dien-3-one butyrate crystallises from ether/diisopropyl ether/hexane; melting point 73°–74°.

EXAMPLE 25

A solution of 1.1 g of 19-hydroxy-20-spiroxa-4,6-dien-3-one butyrate in 18 ml of methanol and 1.8 ml of distilled thioacetic acid is refluxed for 5 hours, 2 ml of water are added, the mixture is stirred for 30 minutes at room temperature, a further 2 ml of water are added and the mixture is stirred overnight at room temperature. The reaction mixture is poured into 300 ml of ice/water and the resulting mixture is stirred for 10 minutes and filtered with suction. The material on the suction filter is dissolved in ethyl acetate and the solution is dried over sodium sulphate and evaporated. The residue is chromatographed on silica gel. Elution with mixtures of hexane/ethyl acetate (9:1) and (3:1) gives a purified product which is taken up in methanol/water and lyophilised; this gives amorphous 7α-acetylthio-19-hydroxy-20-spirox-4-en-3-one butyrate.

EXAMPLE 26

1.5 ml of water, 0.3 g of cadmium carbonate and 0.3 g of mercury chloride are added to a solution of 287 mg of (19R)-3,3-ethylenedithio-19-methyl-20-spirox-4-en-19-ol in 24 ml of acetone and the mixture is stirred at room temperature for 8 hours. For working up, the mixture is filtered through kieselguhr, the material on the filter is washed with acetone and the filtrate is evaporated. The residue is taken up in ethyl acetate and the solution is washed with 1 N hydrochloric acid and ice, then with water and subsequently with a solution of sodium chloride, dried and evaporated. The crude product is chromatographed on silica gel using mixtures of hexane/ethyl acetate (3:1) and (2:1). The (19R)-19-hydroxy-19-methyl-20-spirox-4-en-3-one which is thus obtained is recrystallised from methylene chloride/hexane; melting point 188°–189°.

The starting material is obtained according to Example 20C.

EXAMPLE 27

15 ml of water, 3.0 g of cadmium carbonate and 3.0 g of mercury chloride are added to a solution of 2.9 g of (19S)-3,3-ethylenedithio-19-methyl-20-spirox-4-en-19-ol in 240 ml of acetone and the mixture is stirred at room temperature for 8 hours. For working up, the reaction mixture is filtered through kieselguhr, the material on the filter is washed with acetone, the filtrate is concentrated and the residue is taken up in ethyl acetate. The organic solution is washed with 1 N hydrochloric acid and ice, then with water and subsequently with a solution of sodium chloride, dried and evaporated. The crude product is chromatographed on silica gel using mixtures of hexane/ethyl acetate (3:1) and (2:1) and the (19S)-19-hydroxy-19-methyl-20-spirox-4-en-3-one isolated is further processed without purification.

The starting material is obtained according to Example 20C.

EXAMPLE 28

708 mg of (19S)-19-hydroxy-19-methyl-20-spirox-4-en-3-one are dissolved in 20 ml of acetone, the solution is cooled to an internal temperature of 0° and 0.9 ml of Jones reagent are added and the mixture is stirred for 10 minutes. The excess Jones reagent is decomposed with isopropyl alcohol and the mixture is partitioned between ethyl acetate and water. The organic phase is washed with 1 N sodium bicarbonate solution and with water, dried and evaporated. The crude product is filtered with ether through aluminium oxide (activity level III, neutral) and the 19-methyl-20-spirox-4-ene-3,19-dione isolated is crystallised from ether/diisopropyl ether; melting point 97°-99°.

EXAMPLE 29

0.36 ml of an 8 N solution of chromium trioxide in aqueous sulphuric acid is added to a mixture of 426 mg of 19-hydroxy-20-spirox-4-ene-3,21-dione and 10 ml of acetone, at 0° with stirring. After 10 minutes, the excess Jones reagent is reduced by adding isopropyl alcohol. Water is added to the mixture and the resulting mixture is extracted with ethyl acetate. The organic phase is washed with sodium bicarbonate solution and sodium chloride solution, dried and evaporated in vacuo. The residue, as a solution in toluene/ethyl acetate (4:1), is filtered through 4 g of silica gel and the filtrate is evaporated in vacuo. The residue is freed from impurities by preparative thin layer chromatography on silica gel (PF 254) in the system toluene/acetone (7:3) and crystallised from methylene chloride/ether/acetone. 3,21-Dioxo-20-spirox-4-en-19-al results; melting point 141°-144°.

EXAMPLE 30

1.66 ml of an 8 N solution of chromium trioxide in aqueous sulphuric acid are added to a mixture of 500 mg of 19-hydroxy-20-spirox-4-ene-3,21-dione and 17 ml of acetone, at 0° with stirring. After 30 minutes, excess oxidising agent is decomposed with isopropyl alcohol and the mixture is poured into dilute sodium chloride solution and extracted with ethyl acetate. The extract is washed with dilute sodium chloride solution, dried and evaporated in vacuo at 30°. The residue is dissolved in 17.5 ml of methanol, 175 ml of 3.3 percent strength sodium bicarbonate solution are added and the resulting mixture is washed with ethyl acetate. The aqueous phase is acidified with acetic acid and the product is taken up in ethyl acetate. This ethyl acetate solution is washed with dilute sodium chloride solution, dried and evaporated in vacuo at 30°. The residue is dissolved in 12.5 ml of methylene chloride and an ethereal solution of diazomethane is added until there is a permanent yellow coloration. Excess diazomethane is decomposed with acetic acid and the solution is diluted with methylene chloride, washed with dilute sodium bicarbonate solution and dilute sodium chloride solution, dried and evaporated in vacuo. Crystallisation of the residue from methylene chloride/ether gives methyl 3,21-dioxo-20-spirox-4-en-19-oate; melting point 187°-188.5°.

EXAMPLE 31

In an analogous manner to that described in Example 11A, 2 g of 19-hydroxy-20-spiroxa-4,6-dien-3-one (prepared according to Example 1) are reacted with triphenylmethyl chloride to give 19-trityloxy-20-spiroxa-4,6-dien-3-one. The latter is reacted analogously to the process of Example 11B with trimethylsulphoxonium iodide and sodium hydride in dimethylsulphoxide. The resulting crude 6$\beta$,7$\beta$-methylene-19-trityloxy-20-spirox-4-en-3-one is treated analogously to Example 11C with 80 percent strength acetic acid and freed from the reactant. The crude residue is chromatographed on 90 g of silica gel; 19-hydroxy-6$\beta$,7$\beta$-methylene-20-spirox-4-en-3-one acetate is eluted with a 9:1 mixture of toluene/ethyl acetate; melting point 171°-172.5°. Further elution with a 4:1 mixture of the same solvent gives 19-hydroxy-6$\beta$,7$\beta$-methylene-20-spirox-4-en-3-one; melting point 219°-221°. Both compounds can be recrystallised from methylene chloride/ethyl ether.

EXAMPLE 32

0.17 ml of an 8 N solution of chromium trioxide in aqueous sulphuric acid (Jones reagent) is added to a solution of 200 mg of 19-hydroxy-6$\beta$,7$\beta$-methylene-20-spirox-4-en-3-one in 4.8 ml of acetone, with stirring and ice-cooling. After 10 minutes, the reaction mixture is processed by the procedure described in Example 29 and this results in 6$\beta$,7$\beta$-methylene-3-oxo-20-spirox-4-en-19-al which has a melting point of 130°-131° after recrystallisation from methylene chloride/ethyl ether.

In an analogous manner, 19-hydroxy-6$\beta$,7$\beta$-methylene-20-spirox-4-ene-3,21-dione (Example 11D) gives amorphous 6$\beta$,7$\beta$-methylene-3,21-dioxo-20-spirox-4-en-19-al, the IR spectrum of which has characteristic bands at 1760, 1715, 1660 and 1605 cm$^{-1}$.

EXAMPLE 33

A solution of 120 mg of 19-methyl-20-spirox-4-ene-3,19-dione (for the preparation see Example 28) and 200 mg of chloranil in 12 ml of methanol is refluxed for 3 hours and concentrated. The residue is taken up in ethyl acetate and the solution is washed with a solution of sodium hypersulphite in 1 N sodium hydroxide solution until the aqueous phase remains virtually colourless and is then washed twice with water and once with a solution of sodium chloride, dried and evaporated. The crude 19-methyl-20-spiroxa-4,6-diene-3,19-dione is chromatographed on silica gel using a mixture of hexane/ethyl acetate (3:1) and is isolated from methanol as an amorphous precipitate by adding water.

EXAMPLE 34

In an analogous manner to that described in Example 30, an excess of an ethereal solution of diazomethane is added to a solution of 5.4 g of 3-oxo-20-spiroxa-4,6-dien-19-oic acid (prepared according to Example 3) in 100 ml of methylene chloride and the mixture is further processed. Methyl 3-oxo-20-spiroxa-4,6-dien-19-oate is obtained and after recrystallisation from methylene chloride/hexane this melts at 157°-158°.

EXAMPLE 35

A solution of 2.2 g of 19-hydroxy-20-spiroxa-4,6-dien-3-one in 40 ml of absolute dimethoxyethane is added dropwise at room temperature, in the course of 1 hour, under nitrogen, to a suspension of 700 mg of sodium hydroxide in 50 ml of absolute dimethyl ether and 10 ml of methyl iodide. The reaction mixture is stirred for 3½ hours, the excess sodium hydride is decomposed with methanol and the mixture is poured into water. The product is taken up in ethyl acetate and the organic solution is washed with water and dilute sodium chloride solution, dried and concentrated in vacuo. The residue is chromatographed in a silica gel column; elution with a 9:1 mixture and a 1:1 mixture of hexane/ethyl acetate gives 19-methoxy-20-spiroxa-4,6-dien-3-one, which after recrystallisation from methylene chloride/isopropyl ether melts at 150°–151°.

EXAMPLE 36

The following compounds are obtained in a manner analogous to that in Example 19:
(a) 7α-acetylthio-19-methyl-20-spirox-4-ene-3,19-dione with a melting point of 164°–170° (crystals from methanol/water) from 19-methyl-20-spiroxa-4,6-diene-3,19-dione (see Example 33);
(b) methyl 7α-acetylthio-3-oxo-20-spirox-4-en-19-oate with a melting point of 64°–78° (precipitate from a solution in methanol by the addition of water) from methyl 3-oxo-20-spiroxa-4,6-dien-19-oate; and
(c) 7α-acetylthio-19-methoxy-20-spirox-4-en-3-one with a melting point of 138°–152° (crystals from methylene chloride/isopropyl ether) from 19-methoxy-20-spiroxa-4,6-dien-3-one (see Example 35).

What is claimed is:
1. A 19-oxygenated steroid compound selected from the group consisting of a compound of the spiroxane series of the formula

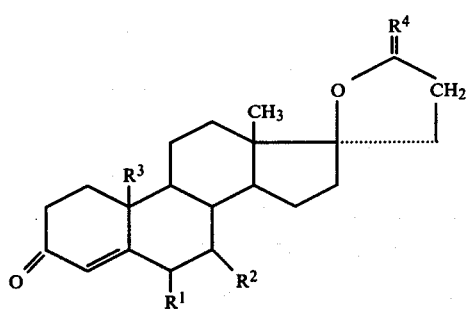

in which $R^1$ is hydrogen and $R^2$ is hydrogen or an α-oriented lower alkanoylthio, or $R^1$ and $R^2$ conjointly are a carbon-carbon bond, α-oriented methylene or β-oriented methylene, $R^3$ is a radical of the partial formula

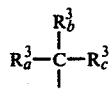

in which $R_a^3$ and $R_b^3$ each individually is hydrogen or lower alkyl, and $R_c^3$ is hydroxyl, esterified hydroxyl or lower alkoxy, or $R_a^3$ and $R_b^3$ conjointly are oxo and $R_c^3$ is hydrogen, lower alkyl, hydroxyl or lower alkoxy, and $R^4$ is two hydrogens or oxo, and of a corresponding 17β-hydroxy-21-carboxylic acid of the formula

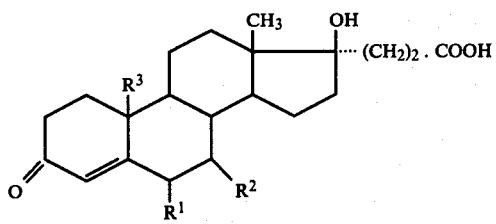

in which $R^1$ and $R^2$ each are hydrogen or conjointly are a C-C bond, an α-oriented methylen or a β-oriented methylene and $R^3$ is as defined above, and a salt thereof, and of a 1,2-dehydro derivative of any of the compounds of the formulae I and IA.

2. A compound according to claim 1, in which $R^3$ is hydroxymethyl or esterified hydroxymethyl.
3. A compound according to claim 2, in which $R^3$ is hydroxymethyl or lower alkanoyloxymethyl.
4. A compound according to claim 1, in which $R^3$ is carboxyl or carboxyl esterified by a lower alkanol.
5. A compound according to claim 4, in which $R^3$ is methoxycarbonyl.
6. A compound according to claim 1, in which $R^1$ is hydrogen and $R^2$ is acetylthio.
7. A compound according to claim 1, in which $R^1$ and $R^2$ conjointly are a β-oriented methylene.
8. A pharmaceutically usable salt of a compound of claim 1.
9. The potassium salt of a compound of claim 1.
10. A compound according to claim 1, which is saturated in the 1,2-position.
11. A compound according to claim 1, which compound is 7α-acetylthio-19-hydroxy-20-spirox-4-en-3-one.
12. A compound according to claim 1, which compound is 7α-acetylthio-19-hydroxy-20-spirox-4-en-3-one acetate.
13. A compound according to claim 1, which compound is 7α-acetylthio-3,21-dioxo-20-spirox-4-en-19-al.
14. A compound according to claim 1, which compound is 19-hydroxy-6β,7-methylene-20-spirox-4-ene-3,21-dione.
15. A compound according to claim 1, which compound is Methyl 7α-acetylthio-3-oxo-20-spirox-4-en-19-oate.
16. A compound according to claim 1, which compound is 19-methyl-20-spiroxa-4,6-diene-3,19-dione.
17. A compound according to claim 1, in which $R^1$ and $R^2$ each is hydrogen.
18. A compound according to claim 17, in which $R^3$ is hydroxymethyl, a lower alkanoyloxymethyl or methoxycarbonyl.
19. A pharmaceutical formulation containing a compound as defined in claim 1, together with a pharmaceutically acceptable carrier.
20. A compound according to claim 3 of the formula I, in which $R^1$ is hydrogen, $R^2$ is acetylthio, and which is saturated in the 1,2-position.
21. A compound according to claim 4 of the formula I, in which $R^1$ is hydrogen, $R^2$ is acetylthio, and which is saturated in the 1,2-position.
22. A compound according to claim 5 of the formula I, in which $R^1$ is hydrogen, $R^2$ is acetylthio, and which is saturated in the 1,2-position.
23. A compound according to claim 3 of the formula I, in which $R^1$ and $R^2$ conjointly are a β-oriented methylene, and which is saturated in the 1,2-position.
24. A compound according to claim 4 of the formula I, in which $R^1$ and $R^2$ conjointly are a β-oriented methylene, and which is saturated in the 1,2-position.
25. A compound according to claim 5 of the formula I, in which $R^1$ and $R^2$ conjointly are a β-oriented methylene, and which is saturated in the 1,2-position.
26. A compound according to claim 6, which is saturated in the 1,2-position.
27. A compound according to claim 7, which is saturated in the 1,2-position.
28. A method for treating hyperaldosteronism in a warm-blooded animal, which comprises administering thereto an effective amount of a compound as defined in claim 1.

* * * * *